United States Patent
Smith

(10) Patent No.: US 6,753,303 B2
(45) Date of Patent: Jun. 22, 2004

(54) WHIPPED COCOA BATH

(75) Inventor: Jennifer Wayland Smith, Harrisburg, PA (US)

(73) Assignee: Hershey Entertainment & Resorts Company, Hershey, PA (US)

( * ) Notice: Subject to any disclaimer, the term of this patent is extended or adjusted under 35 U.S.C. 154(b) by 41 days.

(21) Appl. No.: 10/299,196

(22) Filed: Nov. 19, 2002

(65) Prior Publication Data

US 2003/0109392 A1 Jun. 12, 2003

Related U.S. Application Data

(60) Provisional application No. 60/338,254, filed on Dec. 6, 2001.

(51) Int. Cl.$^7$ ................................................ A61K 7/50
(52) U.S. Cl. ........................ 510/135; 510/130; 510/159; 510/425; 510/428; 510/490; 424/70.1; 424/70.21; 424/70.22; 424/70.27; 424/70.31; 514/775
(58) Field of Search ................................ 510/130, 135, 510/159, 425, 428, 490; 424/70.1, 70.21, 70.22, 70.27, 70.31, 775

(56) References Cited

U.S. PATENT DOCUMENTS

| | | | |
|---|---|---|---|
| 4,153,568 A | | 5/1979 | Light et al. |
| 4,223,018 A | | 9/1980 | Belle |
| 4,384,964 A | | 5/1983 | Boden |
| 4,388,207 A | | 6/1983 | Klemarczyk et al. |
| 4,498,996 A | * | 2/1985 | Klemarczyk ................. 510/107 |
| 4,512,919 A | * | 4/1985 | Wilson et al. ............... 510/102 |
| 4,521,331 A | | 6/1985 | Martel et al. |
| 4,539,143 A | * | 9/1985 | Boden et al. .................. 512/10 |
| 5,053,219 A | * | 10/1991 | Giddey et al. ................. 424/63 |
| 5,059,428 A | | 10/1991 | Wong et al. |
| 5,223,260 A | | 6/1993 | Morgan et al. |
| 5,322,696 A | | 6/1994 | Morgan et al. |
| 5,328,684 A | | 7/1994 | Morgan et al. |
| 5,362,483 A | | 11/1994 | Morgan et al. |
| 5,397,497 A | | 3/1995 | Jakobson et al. |
| 5,474,701 A | | 12/1995 | Jaquess et al. |
| 5,507,952 A | | 4/1996 | Jaquess et al. |
| 5,709,876 A | | 1/1998 | Fuisz |
| 6,172,064 B1 | | 1/2001 | Andrews et al. |
| 6,582,701 B1 | * | 6/2003 | Weber et al. ............. 424/185.1 |

* cited by examiner

*Primary Examiner*—Necholus Ogden
(74) *Attorney, Agent, or Firm*—Carmen Santa Maria; McNees Wallace & Nurick LLC

(57) ABSTRACT

A scented spa bath additive that when added to a spa produces the visual and sensual effects of sitting in a large cocoa bath. The additive is added to the hot water of a spa to produce a chocolate scent and a foaming sensation to provide the user with the sensation of sitting in a hot cocoa bath. The additive is a whipped cocoa bath that not only produces a pleasant chocolate scent, but also produces a bubbly foam that produces a long-lasting froth. Unlike the large bubbles normally produced in spas by adding just a cocoa powder, the whipped cocoa bath of the present invention produces bubbles have a surface tension that allows for a long life, so that the experience can be extended.

23 Claims, No Drawings

WHIPPED COCOA BATH

CROSS-REFERENCE TO RELATED APPLICATIONS

This application claims the benefit of U.S. Provisional Application No. 60/338,254 filed Dec. 6, 2001.

FIELD OF THE INVENTION

The present invention is generally directed to a scented spa bath additive, and specifically to a cocoa-scented spa bath that has an additional effect as a skin softener and regenerator.

BACKGROUND OF THE INVENTION

The legendary beneficial effects of milk on the skin have been part of the lore of history. Legends of Cleopatra taking milk baths to preserve her skin 2000 years ago have been passed on. Of course, the expense of milk and its short life at elevated temperatures has made it impractical for the average person to indulge in such milk baths. The beneficial cosmetic effects of milk and improvements to extend its life have been the subject of modem technology as well. U.S. Pat. No. 5,503,219 ('219 patent) to Giddey et al. describes the beneficial effects of milk products on skin. The '219 patent sets forth the elimination of the problem associated with yellowing of milk-derived products for regeneration and softening of the skin for cosmetic compositions such as shampoos, shaving creams, bath products and shower products. It also teaches that the presence of lactose in milk-derived products, which leads to yellowing, can be eliminated by the addition of $CaCl_2$ to sodium caseinate plus a surfactant to cause milk protein micelles to reform, producing a stable solution having a natural, milky appearance.

The pleasurable olfactory effects of chocolate are also well known. For example, U.S. Pat. No. 4,539,143 ('143 patent) to Boden et al. describes the use of norbornyl pyridine derivatives as a flavor and aroma enhancer. This '143 patent teaches the addition of up to 0.1 parts per million (ppm) of 4-vinylpyridene-methylcyclopentadiene to cocoa mix to provide a long-lasting, natural-like cocoa flavor. The '143 patent also teaches the use of a norbornyl pyridine derivative to cause a cinnamon bitter chocolate aroma and taste profile. The patent does teach the use of these aromas and their derivatives in various products, such as perfumes, creams and deodorants.

U.S. Pat. No. 4,512,919 ('919 patent) to Wilson et al. teaches the use of a 2-methoxy-4-(2-methylpropenyl)phenyl ester of isobutyric acid as an aroma enhancer for use as an olfactory with a bath preparation. The addition of the compound to soap creates a product with chocolate-like undertones that can be added to bath water to produce an aroma having chocolate undertones.

U.S. Pat. No. 4,498,996 ('996 patent) to Klemarczyk, discloses another chemical derivative that can act as either a flavor enhancer or an aroma enhancer. Oxyneopentyl alkanoate derivatives are added to baths to produce an aroma enhancer that can also be a bath additive, while yielding foamed bubbles, but does not produce a bathtub ring. However, this patent does not teach the use of the oxyneopentyl alkanoate derivatives as producing a particular aroma, such as a chocolate aroma.

Likewise, the beneficial effects of spas are also well-known. An entire industry has arisen in which personal spas have been sold to home owners so that individuals can partake of the hot jets of water in the privacy of their homes. Recently, fragrance additives have been made available for addition to these personal spas. Associated with this trend, more elaborate spas have arisen in resorts which include a broad range of services, including various therapies coupled with scented baths.

While these past practices may have been directed at affecting one or two of the senses, such as the senses of smell or touch, what has been lacking is a spa treatment that affects all of the senses with the exception of hearing. The specifically affected senses include sight, smell and feel.

A spa treatment that can provide the beneficial effects to the skin of a milk treatment, while providing the visual and olfactory effects of sitting in a large hot, cup of cocoa has not previously been available. The short life of milk at elevated temperatures has been a problem that has limited the practicality of providing such a cocoa bath. In addition, the use of cocoa in a bath of such a large scale at temperatures that a human being can tolerate, up to about 110° F. does not produce the same aroma as a freshly brewed cup of cocoa, which can range from 130°–200° F. In addition, the lower temperatures of operation of spa fluids prevent the frothy build-up over the surface of the cup of cocoa. Because of these problems, it has not been possible to produce all of the desirable sensory effects of duplicating the experience of sitting in a large cup of cocoa. Nor has such an experience been coupled with the beneficial effects provided by treating the skin with a milk bath. Such beneficial effects are desired to stimulate the senses, which may also reduce tension. It is therefore desirable to produce a spa bath that can simulate the experience of bathing in a large cup of hot cocoa or hot chocolate.

SUMMARY OF THE INVENTION

The present invention is a scented spa bath additive that when added to a spa produces the visual and sensual effects of sitting in a large cocoa bath. The additive is added to the hot water of a spa to produce a chocolate scent and a foaming sensation to provide the user with the sensation of sitting in a hot cocoa bath. The additive is a whipped cocoa bath that not only produces a pleasant chocolate scent, but also produces a bubbly foam that produces a long-lasting froth. Unlike the large bubbles normally produced in spas by adding just a cocoa powder, the whipped cocoa bath of the present invention produces bubbles have a surface tension that allow for a long life, so that the pleasant sensory experience can be extended.

In another embodiment, the present invention is comprised of a solution of cocoa powder, whipped cocoa bath and non-fat dried milk added to spa water. An individual bath typically includes from about 220 gallons of water to about 450 gallons of water. Added to the water is from about ¹⁄₁₆ cup to about ½ cup of cocoa powder (about 0.001–0.018 ounces of cocoa powder per gallon of water), from about ¼ cup to about 1 cup of powdered milk (about 0.004–0.036 ounces of non-fat powdered milk per gallon of water) and about ½ tablespoon to 3 tablespoons of whipped cocoa bath (about 9400:1 to about 230,000:1 water:whipped cocoa bath). The water temperature is maintained within the range of about 90°–110° F. This solution provides not only the visual effect of sitting in a cup of hot cocoa and the olfactory effect of chocolate, but also provides the legendary cosmetic benefits of a milk treatment of the skin. Typically, the additives are increased as the amount of water in the bath is increased.

An advantage of the scented spa additive of the present invention, whipped cocoa bath, is that it provides the beneficial effects of aroma therapy produced by the cocoa scent, as the brain associates the scent of chocolate with the taste of chocolate and the related benefits.

Another advantage of the whipped cocoa bath of the present invention when used in combination with cocoa powder and non-fat dried milk in solution with water is that it additionally provides the benefits to the skin long associated with milk baths.

Still a further advantage of the solution of the present invention is that it produces fine, long-lasting, stable bubbles at typical elevated spa temperatures, in the range of about 90–110° F. that, coupled with the chocolate aroma produce the aura of sitting in a large cup of hot chocolate.

Other features and advantages of the present invention will be apparent from the following more detailed description of the preferred embodiment, taken in conjunction with the accompanying drawings which illustrate, by way of example, the principles of the invention.

DETAILED DESCRIPTION OF THE INVENTION

In one form, the present invention is comprised of cocoa powder, non-fat dried milk, whipped cocoa bath and essence of cocoa added to water, which is maintained at a temperature in the range of about 90–110° F., but preferably is maintained at a temperature in the range of 96°–104° F. and most preferably at about 98° F. About 220 to about 450 gallons of water is added to a standard individual jacuzzi®-like tub such as may be found in a residential bathroom or used in a commercial spa setting. The amount of water may be varied below the 220 gallon level or above the 450 gallon level as conditions dictate, and the amount of ingredients may be adjusted accordingly. The amount of ingredients added should be sufficient to provide the desired effect. More specifically, when the amount of water is varied above or below the preferred amount, or water conditions otherwise dictate (for example, extremely hard water) the amount of powdered milk can be increased or decreased with the amount of water, but the amount of whipped cocoa bath and cocoa powder should be sufficient to produce a pleasant chocolate scent and a bubbly froth producing bubbles with a surface tension that allows for a long life. A long life, as used herein, refers to a time commensurate with the length spent in the spa, typically, at least ten minutes and as long as sixty minutes. The water temperature is either added to the tub at the desired temperature or is brought to the desired temperature by suitable heater and controls. Once the desired temperature within the temperature is reached, cocoa powder is added to the water in the amounts of between about 1/16 cup to about 1/2 cup; about 1/4 cup to about 1 cup of dried, powdered non-fat milk is added and about 1/2 tablespoon to about 3 tablespoons of whipped cocoa bath is added.

In a preferred embodiment of the present invention, about 1/4 cup to about 1/2 cup of dried, powdered milk, about 1/16 cup to about 3/16 cup of cocoa powder and about 1/2 tablespoon to about 1 1/4 tablespoon of whipped cocoa bath is added to about 250 to about 400 gallons of water.

In the most preferred embodiment of the present invention, about 1/8 cup of cocoa powder, about 1/3 cup of dried, non-fat, powdered milk and about one tablespoon of whipped cocoa bath is added to about 270 gallons of water maintained at about 98° F.

The milk is added to provide the skin enhancement effects, such as skin softening. However, as the amount of milk is increased, the bath color will become lighter. The ratio of milk to cocoa powder is important to maintain the color of the water within the desired color range. Too much cocoa powder in relation to the milk provides a bath that is too dark, while too little cocoa powder in relation to the milk produces a bath that is too light. By maintaining the ratios of milk powder, cocoa powder and water within the ranges specified in the preferred embodiment, the desired visual appearance of the bath fairly duplicates that of chocolate. The addition of the whipped cocoa bath enhances the aroma of the bath and provides small, frothy bubbles to simulate the thick foamy froth associated with a cup of hot cocoa.

The cocoa powder is added to provide the characteristic brown coloration of cocoa. It also adds a cocoa scent to the mixture, however the cocoa scent provided solely by cocoa is somewhat subdued.

The whipped cocoa bath provides a number of additional beneficial properties to the spa bath. The whipped cocoa bath includes as a fragrance essence of cocoa, which acts to enhance the olfactory scent contributed by the cocoa powder. The whipped cocoa bath also includes ingredients that improve the visual appearance of the spa bath by providing a frothy bubble effect as well as a dark, pearly appearance somewhat similar to milk chocolate. It is not fully understood at this time, but the addition of the whipped cocoa bath to the powdered milk in the water apparently acts as a surfactant that helps produce the fine, stable bubbles in the bath. The fine stable bubbles produce the sensation of taking a spa bath in a cup of cocoa. The milk also apparently acts in the manner of a detergent in bubble formation to stabilize and reduce the size of the bubbles, without being a detergent. Two additional advantages of the scented spa additive of the present invention are the beneficial effects of the aroma therapy produced by the scent, as the brain associates the scent of chocolate with the taste of chocolate and the related benefits. Additionally, the addition of dried milk to the bath provides benefits to the skin long associated with milk baths. Essence of Cocoa is a product of C, D & P Health Products of Nuttley, N.J.

Bubbles form a thin boundary layer at the surface between water and air. The theory of bubbles is complex and perhaps not completely understood. While this invention is not directed to bubble theory and is not meant to be limited by bubble theory, bubbles will be unstable unless this thin boundary layer can move and absorb pressure variations, thermal variations, and other forces destructive to bubbles as may be found in a spa in which jets are operating. The additive to the water, here primarily the whipped cocoa bath, but also the dried milk and cocoa, must be present in sufficiently high concentrations to exert strong molecular attractions between adjacent molecules, causing strong surface films. The surface tension will vary with the composition of the materials. If the surface tension at the air-water interface is too high, bubbles will collapse into a drop, and if too low, the bubbles will not form at all. The surface tension must be favorable for bubble formation. Bubbles, nevertheless, are metastable at the air-water interface and typically are formed by surfactant molecules having a hydrophobic end and an ionic end. The action of these ends in aligning themselves in the presence of water results in bubble formation. In order for the bubble, once formed, to have a long life, the internal pressure of the bubble must counteract the external forces, which as noted are constantly changing in a hot spa. In a steady state condition, the external pressure is due to air and water acting on the bubble. The external force or pressure of air must be counteracted by the internal pressure of the bubble at the water-bubble interface. This force is determined by $$F_A = (P_i - P_v)\pi r^2,$$

where $P_i$=internal bubble pressure;
$P_V$=external air pressure and
r is the bubble radius.

The external force or pressure of water is provided by the surface tension force downward at the water-bubble interface. This force is determined by $$F_w = 2T(2\pi r)$$

where T is surface tension at the interface.

It is clear from the above that the stability of a bubble in a steady state environment is related to its size or diameter. If the size is too small, it will not be able to withstand the external forces and will collapse into a water droplet. If it becomes too large, its force will exceed the forces counteracting it and it will burst when the molecules can no longer hold together. From the above discussion, it should be clear that finding the correct additive to produce long lasting bubbles, particularly in the presence of other additives such as cocoa, and milk in an active environment such as a spa, is a difficult task, as the art is imprecise.

Whipped cocoa bath is a cleanser that includes water, cocomide DEA, sodium laureth sulfate, cocamidopropyl betaine, glycol stearate, a preselected fragrance such as essence of cocoa, methylparaben, propylparaben, diazolidinyl urea, FD&C blue #1, FD&C red #40 and FD&C yellow #5. Whipped cocoa bath is produced by C, D & P Health Products of Nuttley, N.J. and is available through Hershey Entertainment Company, Hershey, Pa.

Cocomide DEA, which is a diethanolamine from coconut oil, a widely used fatty acid, is an ingredient that is added to the bath to provide foam boosting and to adjust the pH of the foam, the fatty acid generally lowering the pH of spa water. The foam boosting is required to provide the visual aspect of the spa experience that includes sitting in a large vat of hot cocoa.

Sodium laureth sulfate, an ether of $C_{12}H_{25}O_4SN_4$, is a well-known synthetic substance that can be derived from coconut oil. This substance is added both for its ability to cleanse the skin, and for its foam building abilities.

Cocoamidopropyl betaine cannot be adequately represented by a single molecular structure. It is commonly used in shampoos, bubble baths and liquid handsoaps. In the whipped cocoa bath, this ingredient provides good foaming and foam liquid stabilization. It also provides excellent wetting properties, which enhance performance of the bubbles in the spa. It is compatible with anionic, cationic, and nonionic surfactants.

Glycol stearate is an additive that generally provides a pearly, visual effect. However, when used in combination with cocoa powder and powdered milk, the enhancement glycol stearate enhances the chocolate-like hot cocoa visual appeal of the spa bath by providing a sheen to an otherwise flat-looking spa bath. Other additives, such as methylparaben and propylparaben, are preservatives, the methyl form being more soluble in water. When methylparaben and propylparaben are used in combination, they provide broader protection than when used individually. Yet another preservative is diazolidinyl urea. Food colors are added to provide the desired coloration.

The spa bath is created by providing water in the temperature range of about 90°–110° F., but preferably between about 96°–104° F. The non-fat dried milk is added to the hot water, along with the cocoa powder and a suitable quantity of whipped cocoa bath. Although the additives can mix and diffuse naturally to form a solution by the action of the spa in maintaining its temperature, the process of mixing will be accelerated by the action of the jets as the water is pumped through the system when the pump is activated. Fine, frothy, long lasting bubbles will be produced by the solution as it exits the jets. This composition will allow these bubbles to last for at least about thirty minutes within this temperature range. Preferably these small frothy bubbles will maintain sufficient surface tension to last for thirty to sixty minutes in this temperature range.

It is understood that the present invention is directed at a single use, individual bath. The length of the bath is no longer than one hour. The bubbles and the scent produced by the whipped cocoa bath last only for a short time, up to about a half of an hour, after which they begin to dissipate. Although the intended effect is no longer than one-half hour, a larger bath can be prepared by utilizing a larger tub and scaling up the amount of additives within the ranges set forth above to match the volume of water in the larger tub. In this circumstance, a bath can be prepared for a plurality of people.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A composition for use as an additive to a spa bath, the composition comprising:
    cocomide DEA;
    sodium laureth sulfate;
    cocamidopropyl betaine;
    glycol stearate;
    a preselected fragrance;
    methylparaben;
    propylparaben;
    diazolidinyl urea;
    FD&C blue #1;
    FD&C red #40;
    FD&C yellow #5;
    the balance water; and
    wherein the composition, when added in sufficient quantity to water in a spa, produces stable bubbles having a sufficient surface tension to provide for a life of at least ten minutes.

2. The additive composition of claim 1 wherein the bubbles have a life of at least 30 minutes at a spa temperature having a temperature range of about 90–110° F.

3. The additive composition of claim 1 wherein the bubbles have a life of between about 30 minutes and one hour at a spa temperature having a temperature range of about 90–110° F.

4. The additive composition of claim 1 wherein the preselected fragrance is a cocoa fragrance.

5. The additive composition of claim 4 wherein the fragrance is essence of cocoa.

6. The additive composition of claim 1 wherein the composition provides, when added to water in a spa, a pearly visual effect.

7. The additive composition of claim 1 wherein when added in sufficient quantity to water includes a ratio of water to composition from about 35,000:1 to about 210,000:1.

8. A spa water solution comprising:
   a preselected amount of non-fat dried milk;
   a preselected amount of cocoa powder;
   a preselected amount of whipped cocoa bath; and
   the balance water;
   the solution maintained at a temperature in the range of about 90° F. to about 110° F. and characterized by a chocolate scent, and a plurality of long-lasting bubbles so as to produce a visual and olfactory effect of a frothy hot chocolate drink.

9. The spa water solution of claim 7 wherein the whipped cocoa bath includes cocomide DEA, sodium laureth sulfate, cocamidopropyl betaine, glycol stearate, a preselected fragrance, methylparaben, propylparaben, diazolidinyl urea, FD&C blue #1, FD&C red #40 and FD&C yellow #5.

10. The spa water solution of claim 8 wherein the preselected fragrance is essence of cocoa.

11. The spa water solution of claim 7 wherein the solution further comprises from about 220 gallons of water to about 450 gallons of water, from about 1/16 cup to about 1/2 cup of cocoa powder, from about 1/4 cup to about 1 cup of powdered milk and about 1/2 tablespoon to 3 tablespoons of whipped cocoa bath.

12. The spa bath of claim 10 wherein the solution further comprises from about 250 gallons to about 400 gallons of water, from about 1/4 cup to about 1/2 cup of dried, powdered milk, from about 1/16 cup to about 3/16 cup of cocoa powder and from about 1/2 tablespoon to about 1 1/4 tablespoon of whipped cocoa bath.

13. The spa bath of claim 11 wherein the solution further comprises about 270 gallons of water, about 1/8 cup of cocoa powder, about 1/3 cup of dried, non-fat, powdered milk and about one tablespoon of whipped cocoa bath.

14. The spa bath of claim 13 wherein the bath is maintained at a temperature of between about 96°–104° F.

15. The spa bath of claim 12 wherein the bath is maintained at a temperature of about 98° F.

16. The spa water solution of claim 7 wherein the solution further comprises from about 220 gallons of water to about 450 gallons of water, from about 1/16 cup to about 1/2 cup of cocoa powder, from about 1/4 cup to about 1 cup of powdered milk and about 1/2 tablespoon to 3 tablespoons of whipped cocoa bath.

17. A spa solution comprising:
   a preselected amount of dried milk;
   a sufficient amount of cocoa powder to produce a chocolate scent when added to water;
   a sufficient amount of whipped cocoa bath to produce a plurality of long-lasting bubbles so as to provide a frothy visual effect when added to spa water; and
   the balance water;
   the solution maintained at a temperature in the range of about 90° F. to about 110° F., characterized by a simulated effect of a frothy hot chocolate drink.

18. The spa solution of claim 17 wherein a sufficient amount of whipped cocoa bath is about 1/2 to about 3 tablespoons in about 220 gallons to about 450 gallons of water.

19. The spa solution of claim 17 wherein a sufficient amount of whipped cocoa bath further comprises a ratio of water to whipped cocoa powder of about 9400:1 to about 230,000:1.

20. The spa solution of claim 19 wherein the preselected amount of dried milk is about 1/4 to about 1 cup when the water volume is about 220 gallons to about 450 gallons.

21. The spa solution of claim 19 wherein the preselected amount of dried milk comprises a ratio of dried milk to water of about 0.004 ounces per gallon to about 0.036 ounces per gallon.

22. The spa solution of claim 19 wherein the preselected amount of cocoa powder comprises about 1/16 cup to about 1/2 cup when the water volume is about 220 gallons to about 450 gallons.

23. The spa solution of claim 19 wherein the preselected amount of cocoa powder comprises a ratio of cocoa powder to water of about 0.001 ounces per gallon to about 0.018 ounces per gallon.

* * * * *

UNITED STATES PATENT AND TRADEMARK OFFICE
CERTIFICATE OF CORRECTION

PATENT NO. : 6,753,303 B2
DATED : June 22, 2004
INVENTOR(S) : Smith, Jennifer W.

It is certified that error appears in the above-identified patent and that said Letters Patent is hereby corrected as shown below:

Column 1,
Line 23, "modem" should be -- modern --

Signed and Sealed this

Ninth Day of November, 2004

JON W. DUDAS
*Director of the United States Patent and Trademark Office*

UNITED STATES PATENT AND TRADEMARK OFFICE
CERTIFICATE OF CORRECTION

PATENT NO. : 6,753,303 B2
DATED : June 22, 2004
INVENTOR(S) : Smith, Jennifer W.

It is certified that error appears in the above-identified patent and that said Letters Patent is hereby corrected as shown below:

Column 1,
Line 23, "modem" should be -- modern --

Signed and Sealed this

Twenty-second Day of February, 2005

JON W. DUDAS
*Director of the United States Patent and Trademark Office*